(12) United States Patent
Bonnette et al.

(10) Patent No.: US 7,846,175 B2
(45) Date of Patent: Dec. 7, 2010

(54) GUIDEWIRE AND COLLAPSABLE FILTER SYSTEM

(75) Inventors: Michael J. Bonnette, Minneapolis, MN (US); Eric J. Thor, Arden Hills, MN (US); Richard R. Prather, St. Michael, MN (US); Laszlo Trent Farago, Hudson, WI (US)

(73) Assignee: MEDRAD, Inc., Indianola, PA (US)

( * ) Notice: Subject to any disclaimer, the term of this patent is extended or adjusted under 35 U.S.C. 154(b) by 0 days.

(21) Appl. No.: 11/396,732

(22) Filed: Apr. 3, 2006

(65) Prior Publication Data

US 2008/0275485 A1 Nov. 6, 2008

(51) Int. Cl.
*A61M 29/00* (2006.01)

(52) U.S. Cl. ..................................... 606/200

(58) Field of Classification Search .................. 606/200; 623/1.11, 1.12
See application file for complete search history.

(56) References Cited

U.S. PATENT DOCUMENTS

| | | | |
|---|---|---|---|
| 1,902,418 A | 3/1933 | Pilgrim | |
| 4,385,635 A | 5/1983 | Ruiz | |
| 4,619,246 A | 10/1986 | Molgaard-Nielsen et al. | |
| 4,690,672 A | 9/1987 | Veltrup | |
| 4,790,812 A | 12/1988 | Hawkins, Jr. et al. | |
| 4,790,813 A | 12/1988 | Kensey | |
| 4,873,978 A | 10/1989 | Ginsburg | |
| 4,898,574 A | 2/1990 | Uchiyma et al. | |
| 4,913,698 A | 4/1990 | Ito et al. | |
| 4,921,484 A | 5/1990 | Hillstead | |
| 4,997,435 A | 3/1991 | Demeter | |
| 4,998,539 A | 3/1991 | Delsanti | |
| 5,064,428 A | 11/1991 | Cope et al. | |
| 5,071,407 A | 12/1991 | Termin et al. | |
| 5,102,415 A | 4/1992 | Guenther et al. | |
| 5,114,399 A | 5/1992 | Lovalcheck | |
| 5,152,777 A | 10/1992 | Goldberg et al. | |
| 5,215,614 A | 6/1993 | Wijkamp et al. | |
| 5,221,270 A | 6/1993 | Parker | |
| 5,234,416 A | 8/1993 | Macaulay et al. | |
| 5,250,059 A | 10/1993 | Andreas et al. | |
| 5,259,842 A | 11/1993 | Plechinger et al. | |
| 5,300,022 A | 4/1994 | Klapper et al. | |
| 5,318,518 A | 6/1994 | Plechinger et al. | |

(Continued)

FOREIGN PATENT DOCUMENTS

EP 0293605 12/1988

(Continued)

OTHER PUBLICATIONS

F.A.S.T. Funnel Catheter, Proximal Occlusion Embolectomy/Thrombectomy System, Genesis Medical Interventional, Inc.; Product literature pp. 1-4.

(Continued)

*Primary Examiner*—Todd E Manahan
*Assistant Examiner*—Lindsey Bachman
(74) *Attorney, Agent, or Firm*—David Schramm

(57) ABSTRACT

A guidewire with collapsible filter system where a deployable, collapsible and retrievable filter attached to a guidewire tube is utilized for filtering thrombotic particulate from blood flow in the vascular system during thrombectomy or other interventional vascular procedures.

11 Claims, 10 Drawing Sheets

U.S. PATENT DOCUMENTS

| | | | |
|---|---|---|---|
| 5,350,398 A | 9/1994 | Pavenik et al. |
| 5,358,485 A | 10/1994 | Vance et al. |
| 5,370,609 A | 12/1994 | Drasler et al. |
| 5,380,307 A | 1/1995 | Chee et al. |
| 5,419,774 A | 5/1995 | Willard et al. |
| 5,425,723 A | 6/1995 | Wang et al. |
| 5,456,667 A | 10/1995 | Ham et al. |
| 5,496,267 A | 3/1996 | Drasler et al. |
| 5,496,277 A | 3/1996 | Termin et al. |
| 5,496,330 A | 3/1996 | Bates et al. |
| 5,549,626 A | 8/1996 | Miller et al. |
| 5,681,336 A | 10/1997 | Clement et al. |
| 5,713,849 A | 2/1998 | Bosma et al. |
| 5,720,764 A | 2/1998 | Naderlinger |
| 5,792,167 A | 8/1998 | Kablik et al. |
| 5,843,022 A | 12/1998 | Willard et al. |
| 5,908,435 A | 6/1999 | Samuels |
| 5,944,686 A | 8/1999 | Patterson et al. |
| 5,947,995 A | 9/1999 | Samuels |
| 5,989,210 A | 11/1999 | Morris et al. |
| 6,001,118 A | 12/1999 | Daniel et al. |
| 6,022,336 A | 2/2000 | Zadno-Azizi et al. |
| 6,042,598 A | 3/2000 | Tsugita et al. |
| 6,066,149 A | 5/2000 | Samson et al. |
| 6,080,170 A | 6/2000 | Nash et al. |
| 6,096,001 A | 8/2000 | Drasler et al. |
| 6,129,697 A | 10/2000 | Drasler et al. |
| 6,129,698 A | 10/2000 | Beck |
| 6,129,739 A | 10/2000 | Khosravi |
| 6,135,977 A | 10/2000 | Drasler et al. |
| 6,135,991 A | 10/2000 | Muni et al. |
| 6,152,946 A * | 11/2000 | Broome et al. | 606/200 |
| 6,159,230 A | 12/2000 | Samuels |
| 6,168,622 B1 | 1/2001 | Mazzocchi |
| 6,171,328 B1 | 1/2001 | Addis |
| 6,179,860 B1 | 1/2001 | Fulton, III et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,221,006 B1 | 4/2001 | Dubrul et al. |
| 6,224,570 B1 | 5/2001 | Le et al. |
| 6,238,412 B1 | 5/2001 | Dubrul et al. |
| 6,258,115 B1 | 7/2001 | Dubrul |
| 6,258,120 B1 | 7/2001 | McKenzie et al. |
| 6,290,710 B1 | 9/2001 | Cryer et al. |
| 6,325,815 B1 | 12/2001 | Kusleika et al. |
| 6,325,816 B1 | 12/2001 | Fulton, III et al. |
| 6,361,546 B1 | 3/2002 | Khosravi |
| 6,364,895 B1 | 4/2002 | Greenhalgh |
| 6,368,338 B1 | 4/2002 | Konya et al. |
| 6,371,970 B1 | 4/2002 | Khosravi et al. |
| 6,371,971 B1 | 4/2002 | Tsugita et al. |
| 6,375,635 B1 | 4/2002 | Moutafis et al. |
| 6,383,193 B1 | 5/2002 | Cathcart et al. |
| 6,383,206 B1 | 5/2002 | Gillick et al. |
| 6,395,014 B1 | 5/2002 | Macoviak et al. |
| 6,409,742 B1 | 6/2002 | Fulton, III et al. |
| 6,436,121 B1 | 8/2002 | Blom |
| 6,443,926 B1 | 9/2002 | Kletschka |
| 6,450,989 B2 | 9/2002 | Dubrul et al. |
| 6,499,487 B1 | 12/2002 | McKenzie et al. |
| 6,511,492 B1 | 1/2003 | Rosenbluth et al. |
| 6,517,559 B1 | 2/2003 | O'Connell |
| 6,530,923 B1 | 3/2003 | Dubrul et al. |
| 6,530,935 B2 | 3/2003 | Wensel et al. |
| 6,530,939 B1 | 3/2003 | Hopkins et al. |
| 6,544,279 B1 | 4/2003 | Hopkins et al. |
| 6,558,405 B1 | 5/2003 | McInnes |
| 6,558,406 B2 | 5/2003 | Okada |
| 6,562,058 B2 | 5/2003 | Seguin et al. |
| 6,589,263 B1 | 7/2003 | Hopkins et al. |
| 6,602,204 B2 | 8/2003 | Dubrul et al. |
| 6,602,265 B2 | 8/2003 | Dubrul et al. |
| 6,610,077 B1 | 8/2003 | Hancock et al. |
| 6,616,679 B1 | 9/2003 | Khosravi et al. |
| 6,635,070 B2 * | 10/2003 | Leeflang et al. | 606/200 |
| 6,656,203 B2 | 12/2003 | Roth et al. |
| 6,673,089 B1 | 1/2004 | Yassour et al. |
| 6,676,637 B1 | 1/2004 | Bonnette et al. |
| 6,685,722 B1 | 2/2004 | Rosenbluth et al. |
| 6,695,813 B1 | 2/2004 | Boyle et al. |
| 6,695,858 B1 | 2/2004 | Dubrul et al. |
| 6,695,865 B2 | 2/2004 | Boyle et al. |
| 6,699,260 B2 | 3/2004 | Dubrul et al. |
| 6,712,834 B2 | 3/2004 | Yassour et al. |
| 6,712,835 B2 | 3/2004 | Mazzoucchi et al. |
| 6,719,718 B2 | 4/2004 | Bonnette |
| 6,740,112 B2 | 5/2004 | Yodfat et al. |
| 6,743,247 B1 | 6/2004 | Levinson et al. |
| 6,758,855 B2 | 7/2004 | Fulton, III et al. |
| 6,761,727 B1 | 7/2004 | Ladd |
| 6,783,538 B2 | 8/2004 | McGuckin, Jr. et al. |
| 6,818,006 B2 | 11/2004 | Douk et al. |
| 6,974,468 B2 | 12/2005 | DoBrava et al. |
| 7,011,654 B2 | 3/2006 | Dubrul et al. |
| 7,037,321 B2 | 5/2006 | Sachdeva et al. |
| 7,108,677 B2 | 9/2006 | Courtney et al. |
| 7,174,636 B2 | 2/2007 | Lowe |
| 7,220,269 B1 | 5/2007 | Ansel et al. |
| 7,232,432 B2 | 6/2007 | Fulton, III et al. |
| 7,303,575 B2 | 12/2007 | Ogle |
| 7,331,980 B2 | 2/2008 | Dubrul et al. |
| 7,399,308 B2 | 7/2008 | Borillo et al. |
| 7,410,491 B2 | 8/2008 | Hopkins et al. |
| 7,422,579 B2 | 9/2008 | Wahr et al. |
| 7,479,152 B2 | 1/2009 | Fulton, III et al. |
| 7,491,210 B2 | 2/2009 | Dubrul et al. |
| 2002/0045916 A1 | 4/2002 | Gray et al. |
| 2002/0111647 A1 | 8/2002 | Khairkhahan et al. |
| 2002/0151927 A1 | 10/2002 | Douk et al. |
| 2002/0161392 A1 | 10/2002 | Dubrul |
| 2002/0161394 A1 | 10/2002 | Macoviak et al. |
| 2002/0169474 A1 | 11/2002 | Kusleika et al. |
| 2003/0004540 A1 | 1/2003 | Linder et al. |
| 2003/0004541 A1 | 1/2003 | Linder et al. |
| 2003/0065355 A1 | 4/2003 | Weber |
| 2003/0109896 A1 | 6/2003 | Dubrul et al. |
| 2003/0120304 A1 | 6/2003 | Kaganov et al. |
| 2003/0176884 A1 * | 9/2003 | Berrada et al. | 606/200 |
| 2003/0176886 A1 | 9/2003 | Wholey et al. |
| 2003/0195537 A1 | 10/2003 | Dubrul et al. |
| 2003/0199890 A1 | 10/2003 | Dubrul et al. |
| 2003/0208226 A1 | 11/2003 | Bruckheimer et al. |
| 2003/0208227 A1 | 11/2003 | Thomas |
| 2003/0212361 A1 | 11/2003 | Boyle et al. |
| 2003/0212432 A1 | 11/2003 | Khairkhahan et al. |
| 2003/0216774 A1 | 11/2003 | Larson |
| 2003/0229374 A1 | 12/2003 | Brady et al. |
| 2004/0010206 A1 | 1/2004 | Dubrul et al. |
| 2004/0064179 A1 | 4/2004 | Linder et al. |
| 2004/0093011 A1 | 5/2004 | Vrba |
| 2004/0116831 A1 | 6/2004 | Vrba |
| 2004/0122468 A1 | 6/2004 | Yodfat et al. |
| 2004/0133232 A1 | 7/2004 | Rosenbluth et al. |
| 2004/0199202 A1 | 10/2004 | Dubrul et al. |
| 2004/0220609 A1 | 11/2004 | Douk et al. |
| 2004/0230286 A1 | 11/2004 | Moore et al. |
| 2004/0236369 A1 | 11/2004 | Dubrul |
| 2004/0260332 A1 | 12/2004 | Dubrul et al. |
| 2004/0260333 A1 | 12/2004 | Dubrul et al. |
| 2005/0021075 A1 | 1/2005 | Bonnette et al. |
| 2005/0033172 A1 | 2/2005 | Dubrul et al. |
| 2005/0055048 A1 * | 3/2005 | Dieck et al. | 606/200 |
| 2005/0090845 A1 | 4/2005 | Boyd |

| | | | |
|---|---|---|---|
| 2005/0096728 A1 | 5/2005 | Ramer | |
| 2005/0251246 A1 | 11/2005 | Dubrul et al. | |
| 2005/0267516 A1 | 12/2005 | Soleimani et al. | |
| 2005/0277976 A1 | 12/2005 | Galdonik et al. | |
| 2005/0283186 A1* | 12/2005 | Berrada et al. ............ | 606/200 |
| 2006/0015138 A1 | 1/2006 | Gertner | |
| 2006/0030877 A1 | 2/2006 | Martinez et al. | |
| 2006/0058832 A1 | 3/2006 | Melzer et al. | |
| 2006/0058837 A1 | 3/2006 | Bose et al. | |
| 2006/0167491 A1 | 7/2006 | Wholey et al. | |
| 2006/0189921 A1 | 8/2006 | Galdonik et al. | |
| 2006/0241676 A1 | 10/2006 | Johnson et al. | |
| 2008/0015541 A1 | 1/2008 | Rosenbluth et al. | |
| 2008/0015628 A1 | 1/2008 | Dubrul et al. | |
| 2008/0109031 A1 | 5/2008 | Sepetka et al. | |
| 2008/0109088 A1 | 5/2008 | Galdonik et al. | |

FOREIGN PATENT DOCUMENTS

| | | |
|---|---|---|
| EP | 0411118 | 2/1991 |
| EP | 0472334 | 2/1992 |
| EP | 0533511 | 3/1993 |
| EP | 1127556 | 8/2001 |
| EP | 1987787 | 11/2008 |
| FR | 2580-504 | 10/1986 |
| FR | 2666980 | 3/1992 |
| FR | 2694687 | 2/1994 |
| FR | 2768326 | 3/1999 |
| WO | 8809683 | 12/1988 |
| WO | 9203097 | 3/1992 |
| WO | 9414389 | 7/1994 |
| WO | 9424956 | 11/1994 |
| WO | 9717100 | 5/1997 |
| WO | 9727808 | 8/1997 |
| WO | 9742879 | 11/1997 |
| WO | 9802084 | 1/1998 |
| WO | 9802112 | 1/1998 |
| WO | 9823322 | 6/1998 |
| WO | 9833443 | 8/1998 |
| WO | 9838920 | 9/1998 |
| WO | 9839053 | 9/1998 |
| WO | 9849952 | 11/1998 |
| WO | 9850103 | 11/1998 |
| WO | 9851237 | 11/1998 |
| WO | 9922673 | 5/1999 |
| WO | 9923976 | 5/1999 |
| WO | 9925252 | 5/1999 |
| WO | 9940964 | 8/1999 |
| WO | 9942059 | 8/1999 |
| WO | 9944510 | 9/1999 |
| WO | 9944542 | 9/1999 |
| WO | 0007655 | 2/2000 |
| WO | 0016705 | 3/2000 |
| WO | 0049970 | 8/2000 |
| WO | 0108595 | 2/2001 |
| WO | 0108596 | 2/2001 |
| WO | 0110320 | 2/2001 |
| WO | 0115629 | 3/2001 |
| WO | 0121077 | 3/2001 |
| WO | 0121100 | 3/2001 |
| WO | 0126726 | 4/2001 |
| WO | 0135857 | 5/2001 |
| WO | 0143662 | 6/2001 |
| WO | 0149208 | 7/2001 |
| WO | 0149215 | 7/2001 |
| WO | 0149355 | 7/2001 |
| WO | 0152768 | 7/2001 |
| WO | 0158382 | 8/2001 |
| WO | 0160442 | 8/2001 |
| WO | 0187183 | 11/2001 |
| WO | 0189413 | 11/2001 |
| WO | 0222046 | 3/2002 |
| WO | 02060519 | 8/2002 |

OTHER PUBLICATIONS

Cordis, Precise Nitinol Stent System, Cordis ANGIOGUARD Emboli Capture Guidewire, "A Patient's Guide to Disease in the Carotid Arteries". pp. 13 & 18; Dec. 2004.

Understanding Carotid Artery Stenting, Patient Information Guide, Boston Scientific; p. 4 ; 2008.

"A Novel, Low-Profile Filter-Wire (Interceptor) Embolic Protection Device During Saphenous Vein Graft Stenting", Young, MD, et al.; pp. 511-514; The American Journal of Cardiology vol. 95, Feb. 15, 2005.

U.S. Appl. No. 10/958,509, filed Oct. 5, 2004, "Filter With Guidewire and Method of Use", Bonnette.

"Filter Devices for Cerebral Protection During Carotid Angioplasty and Stenting", Kasirajan, MD et al., J. Endovasc Ther 2003; 10: 1039-1045.

International Search Report issued Oct. 27, 2008 in related International Patent Application PCT/US08/81310.

International Search Report issued Oct. 2, 2008 in related International Patent Application PCT/US08/66046.

Non-Final Rejection issued Oct. 1, 2009 in corresponding U.S. Appl. No. 11/811,974.

* cited by examiner

GUIDEWIRE AND COLLAPSABLE FILTER SYSTEM

CROSS REFERENCES TO RELATED APPLICATIONS

None.

BACKGROUND OF THE INVENTION

1. Field of the Invention

The present invention relates to catheters, and more directly pertains to a deployable, collapsible and retrievable filter attached to a guidewire which is tubular for filtering of blood in the vascular system during thrombectomy or other interventional vascular procedures.

2. Description of the Prior Art

Arterial disease involves damage that happens to the arteries in the body. Diseased arteries can become plugged with thrombus, plaque, or grumous material that may ultimately lead to a condition known as ischemia. Ischemia refers to a substantial reduction or loss of blood flow to the heart muscle or any other tissue that is being supplied by the artery and can lead to permanent damage of the affected region. While arterial disease is most commonly associated with the formation of hard plaque and coronary artery disease in the heart, similar damage can happen to many other vessels in the body, such as the peripheral vessels and cerebral vessels, due to the buildup of hard plaque or softer thrombus or grumous material within the lumen of an artery or vein.

A variety of vascular medical devices and procedures have been developed to treat diseased vessels. The current standard procedures include bypass surgery (where a new blood vessel is grafted around a narrowed or blocked artery), and several different types of nonsurgical interventional vascular medical procedures, including angioplasty (where a balloon on a catheter is inflated inside a narrowed or blocked portion of an artery in an attempt to push back plaque or thrombotic material), stenting (where a metal mesh tube is expanded against a narrowed or blocked portion of an artery to hold back plaque or thrombotic material), and debulking techniques in the form of atherectomy (where some type of high speed or high power mechanism is used to dislodge hardened plaque) or thrombectomy (where some type of mechanism or infused fluid is used to dislodge grumous thrombotic material). In each of these interventional vascular medical procedures, a very flexible guidewire is routed through the patient's vascular system to a desired treatment location, and then a catheter that includes a device on the distal end appropriate for the given procedure is tracked along the guidewire to the treatment location.

Although interventional vascular procedures avoid many of the complications involved in surgery, there is a possibility of complications if some of the plaque, thrombus or other material breaks free and flows downstream in the artery or other vessel, potentially causing a stroke, a myocardial infarction (heart attack), or other tissue death. One solution to this potential complication is to use some kind of occlusive device or filtering device to block or screen the blood flowing downstream of the treatment location.

The use of a protective device in the form of an occlusive device or filtering device as part of a vascular procedure is becoming more common in debulking procedures performed on heart bypass vessels. Most heart bypass vessels are harvested and transplanted from the saphenous vein located along the inside of the patient's leg. The saphenous vein is a long straight vein that has a capacity more than adequate to support the blood flow needs of the heart. Once transplanted, the saphenous vein is subject to a buildup of plaque or thrombotic materials in the grafted arterial lumen. Unfortunately, the standard interventional vascular treatments for debulking are only moderately successful when employed to treat saphenous vein coronary bypass grafts. The complication rate for a standard balloon angioplasty procedure in a saphenous vein coronary bypass graft is higher than in a native vessel with the complications including embolization, "no reflow" phenomena, and procedurally related myocardial infarction. Atherectomy methods including directional, rotational, and laser devices are also associated with a high degree of embolization resulting in a greater likelihood of infarction. The use of stents for saphenous vein coronary bypass grafts has produced mixed results. Stents provide for less restenosis, but they do not eliminate the risk of embolization and infarction incurred by standard balloon angioplasty.

In order to overcome the shortcomings of these standard nonsurgical interventional treatments in treating saphenous vein coronary bypass graft occlusion, embolic protection methods utilizing a protective device distal to the lesion have been developed. The protective device is typically a filter or a balloon. Use of a protective device in conjunction with an atherectomy or thrombectomy device is intended to prevent emboli from migrating beyond the protective device and to allow the embolic particles to be removed, thereby subsequently reducing the risk of myocardial infarction. When the protective device is a balloon, the balloon is inserted and inflated at a point distal to the treatment site or lesion site. Therapy is then performed at the site and the balloon acts to block all blood flow, which prevents emboli from traveling beyond the balloon. Following treatment, some form of particle removal device must be used to remove the dislodged emboli prior to balloon deflation. U.S. Pat. No. 5,843,022 uses a balloon to occlude the vessel distal to a lesion or blockage site. The occlusion is treated with a high pressure water jet, and the fluid and entrained emboli are subsequently removed via an extraction tube. U.S. Pat. No. 6,135,991 describes the use of a balloon to occlude the vessel allowing blood flow and pressure to prevent the migration of emboli proximally from the treatment device. While effective as a protective device, a balloon may result in damaged tissue due to lack of blood flow downstream of the treatment area due to the time required to inflate and deflate the balloon.

To overcome this disadvantage, most development in relation to occlusive devices has focused on devices that screen the blood through a filter arrangement. An early arterial filtering system utilizing a balloon catheter with a strainer device is described in U.S. Pat. No. 4,873,978. The strainer device is inserted into a vessel downstream of the treatment site. The strainer device responds to actuation of a separately introduced control cable to open and close a plurality of tines capable of retaining dislodged particles. After treatment, the strainer device is collapsed and the entrapped emboli are removed from the body. The additional wire, however, creates additional complexity for the user.

More recently, filter designs have been deployed through the use of a single guidewire in which the filter device is transported to the deployment area within a sheath or catheter. Typical filters have either an umbrella shape to capture emboli or a tube shape in which the proximal end contains larger openings than the distal end so as to allow the blood and debris to enter the filter. The filter thus presents an operational face to the flow of blood within the vessel as provided by the distal end of the tubular filter that is concave in orientation.

Particles are captured within the concave face of the filter and are then retracted out of the vessel when the entire device is removed from the body.

One of the challenges regarding filters is the manner in which it is transported to and from the area of interest. U.S. Pat. Nos. 6,042,598, 6,361,546, 6,371,970, 6,371,971 and 6,383,206 describe various examples of filter arrangements that are to be deployed through a sheath, while U.S. Pat. Nos. 6,080,170, 6,171,328, 6,203,561, 6,364,895 and 6,325,815 describe filters that are deployed by a catheter. For example, U.S. Pat. No. 6,371,971 describes a blood filter positioned by way of a single guidewire covered by a sheath for advancement through the channel. The sheath compresses the struts of the filter while in transit. An interventional procedure requires deployment of the sheath along a guidewire downstream of the vascular occlusion. The sheath is retracted and the filter expands to a predetermined size. The filter is retrieved after the procedure by deploying the sheath back down the guidewire, capturing the filter and removing the system from the patient. The disadvantage associated with this type of filter is that re-insertion of the sheath for the collapsing and removal of the filter offers an opportunity to damage the vessel during additional routing and during removal.

Another disadvantage associated with many prior art filters is that dislodged or loosened thrombotic particulate is successfully filtered by the filter, but remains in the filter to clog the filter to the flow of blood through the filter. Additionally, thrombotic particulate which may cling to the filter or which is in loose association with the filter may be lost into the vasculature during retraction of the filter. Thrombotic particulate which is lodged within the filter mesh can hamper suitable collapsing of the filter for removal due to the additional bulk. Ideally, cleansing of the filter by a thrombectomy catheter, such as an Angiojet®, during the procedure would be desirable, but often structure which is incorporated to maintain the opening at the proximal end of the filter could prohibit or interfere with introduction of the thrombectomy catheter therein for the purpose of such cleansing, wherein thrombotic particulate is dislodged from the filter and urged proximally within the thrombectomy catheter as waste product.

There is a need then for a protective device capable of embolization protection for vascular and arterial procedures without the design limitations of the existing approaches. Occlusive balloons can remain in place too long, increasing the risk of vessel damage downstream of the occlusion. Protective filters avoid this problem but suffer from complicated deployment structures and retraction schemes and from introduction of particulate matter into the vasculature due to operational considerations. Moreover, existing filters are limited in range due to the filter support framework, which also may result in vessel damage.

It would be desirable to provide an occlusive filter device on a guidewire which collapses to a reduced and thin profile which facilitates removal of thrombotic particulate matter which is engaged by such a protective occlusive filter. It would also be desirable to provide a protective occlusive filter device as part of a guidewire which is accessibly cleansable and thereby facilitates removal of thrombotic particulate matter which is engaged by such a protective occlusive filter.

SUMMARY OF THE INVENTION

The general purpose of the present invention is to provide a stand-alone guidewire with collapsible filter system for filtration of fragmented thrombus or other particulate from the blood stream wherein a guidewire with collapsible filter is placed and positioned within the vasculature. Although use of the stand-alone system of the invention is described in association with thrombectomy catheter devices, part or all of the guidewire with collapsible filter system can be incorporated into use with other procedures or medical components.

According to one embodiment of the present invention, herein referred to as a guidewire with collapsible filter system, there is a guidewire with collapsible filter and a delivery sheath. The guidewire with collapsible filter includes a fine mesh flexible filter of nitinol or other suitable material secured over and about the distal portion of a guidewire which is tubular. The shape of the collapsible filter exhibits shape memory, i.e., when unrestrained the shape of the collapsible filter returns to the original shape determined during fabrication, whereby such a shape is compressibly suitable for automatic deployed expansion from within a delivery sheath within and into a blood vessel or like vascular region for filtration of particulate caused by thrombectomy or other procedures. The guidewire with collapsible filter is loaded into the delivery sheath for delivery of the collapsible filter to and beyond a thrombus site in a blood vessel. During loading, the filter, being extremely flexible, is compressed by the lumen of the delivery sheath to conform to the geometry of the lumen and is positioned to reside within the distal portion of the delivery sheath. The distal end of the guidewire and attached compressed collapsible filter, mostly located in the delivery sheath, are then advanced, preferably unitarily, to and slightly beyond a thrombus site in the vasculature. At the desired position, the guidewire and attached compressed collapsible filter are revealed by retracting the delivery sheath proximally, whereupon the collapsible filter is automatically deployed therefrom in outwardly directed expansion attempting to maintain the memory shape. Such expansion causes intimate contact of the vessel wall by the expanding collapsible filter, whereby the collapsible filter is then incorporated in a general filtration process whereby thrombus, plaque or grumous materials are trapped by the collapsible filter. Loosened, macerated and exhausted particulate from a thrombectomy catheter, if used, can also be filtered.

Removal of the guidewire with collapsible filter is accomplished by reshaping of the collapsible filter in order to withdraw the guidewire with collapsible filter from the vasculature. A small operator accessible cord extends from the proximal end of the guidewire and distally through a guidewire lumen to loosely and freely exit the lumen just proximal to the region of attachment of the collapsible filter to the guidewire. The cord is routed in close proximity to the collapsible filter interior to extend to near the annular edge of the collapsible filter where the cord is loosely woven in close proximity to the annular edge of the collapsible filter and otherwise secured thereto. A slot, preferably filled with frangible material or configured otherwise in a suitable manner, extends along the distal portion of the guidewire to provide a path for the cord when forcibly actuated for the purpose of collapsibly reshaping the collapsible filter. Collapsing and reshaping of the collapsible filter is accomplished by forcibly actuating the cord proximally, whereby the distal portion of the cord forcibly parts the frangible material in the slot and exerts proximally directed force about the annular peripheral proximal end of the collapsible filter whereby the peripheral proximal end of the collapsible filter is contractingly drawn inwardly and simultaneously stretched proximally along the distal portion of the guidewire, thus reducing the cross section of the collapsible filter. The collapsed collapsible filter, which may include thrombotic or other particulate, and guidewire can then be unitarily urged proximally for removal through the vasculature and point of entry. Alternatively, removal can be accomplished by use of the delivery sheath or other catheter device. During removal of the guidewire with collapsible filter, fluid flow is maintained to exhaust the thrombotic or other particulate stopped by the filter to prevent flow distally along the vasculature, or in the alternative, suction may be applied to the thrombectomy catheter to assist in particulate removal.

One significant aspect and feature of the present invention is a guidewire having a collapsible filter attached at a distal location on the guidewire.

Another significant aspect and feature of the present invention is a guidewire having a collapsible filter attached at a distal location on the guidewire which can operate as a stand-alone device.

Another significant aspect and feature of the present invention is a guidewire having a collapsible filter which can be used with existing thrombectomy catheters.

Still another significant aspect and feature of the present invention is the use of a collapsible filter which is elastic and conformal in shape and which is flexible generally along and about a central longitudinal axis, as well as radially about a central longitudinal axis.

Yet another significant aspect and feature of the present invention is a guidewire with collapsible filter in cooperation with a delivery sheath each of which can be maneuvered to place the collapsible filter at a location distal to a thrombus site.

A further significant aspect and feature of the present invention is a guidewire and collapsible filter wherein the collapsible filter is automatically and expandingly deployable to sealingly and conformingly contact the interior wall of a blood vessel.

A still further significant aspect and feature of the present invention is a guidewire with collapsible filter in which the collapsible filter has compressible, collapsible, and self-expandable geometry.

A still further significant aspect and feature of the present invention is a guidewire with collapsible filter, the collapsible filter being compressionally configured for distal passage through and beyond a delivery sheath and thence automatically and expandingly self-reconfigured for intimate contact with the interior of a blood vessel for the primary purposes of filtration of thrombotic particulate and the passage of blood therethrough.

A still further significant aspect and feature of the present invention is a guidewire with collapsible filter including a cord extending along a guidewire lumen for use in forcibly collapsing, elongating, reducing of the shape and profile of the collapsible filter subsequent to deployment and use.

Yet another significant aspect and feature of the present invention is a guidewire with collapsible filter wherein the filter can include one or more mesh or woven filtration layers.

A still further significant aspect and feature of the present invention is a guidewire with collapsible filter which filters thrombotic particulate but allows the passage of blood therethrough.

Still another significant aspect and feature of the present invention is a guidewire with collapsible filter which can be alternatively operated in cooperation with a thrombectomy catheter to filter thrombotic particulate, whereby the thrombectomy catheter actively removes filtered thrombotic particulate from the expanded collapsible filter interior face and actively urges such thrombotic particulate proximally for disposal through the thrombectomy catheter.

Yet another significant aspect and feature of the present invention is a guidewire with collapsible filter which can be retracted through a catheter by itself or can be retracted into the catheter, whereby the combined filter and guidewire and catheter can be removed as a unit.

Having thus briefly described an embodiment of the present invention and having set forth some significant aspects and features of the present invention, it is the principal object of the present invention to provide a guidewire with collapsible filter system and method of use.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENT

Figure 1:
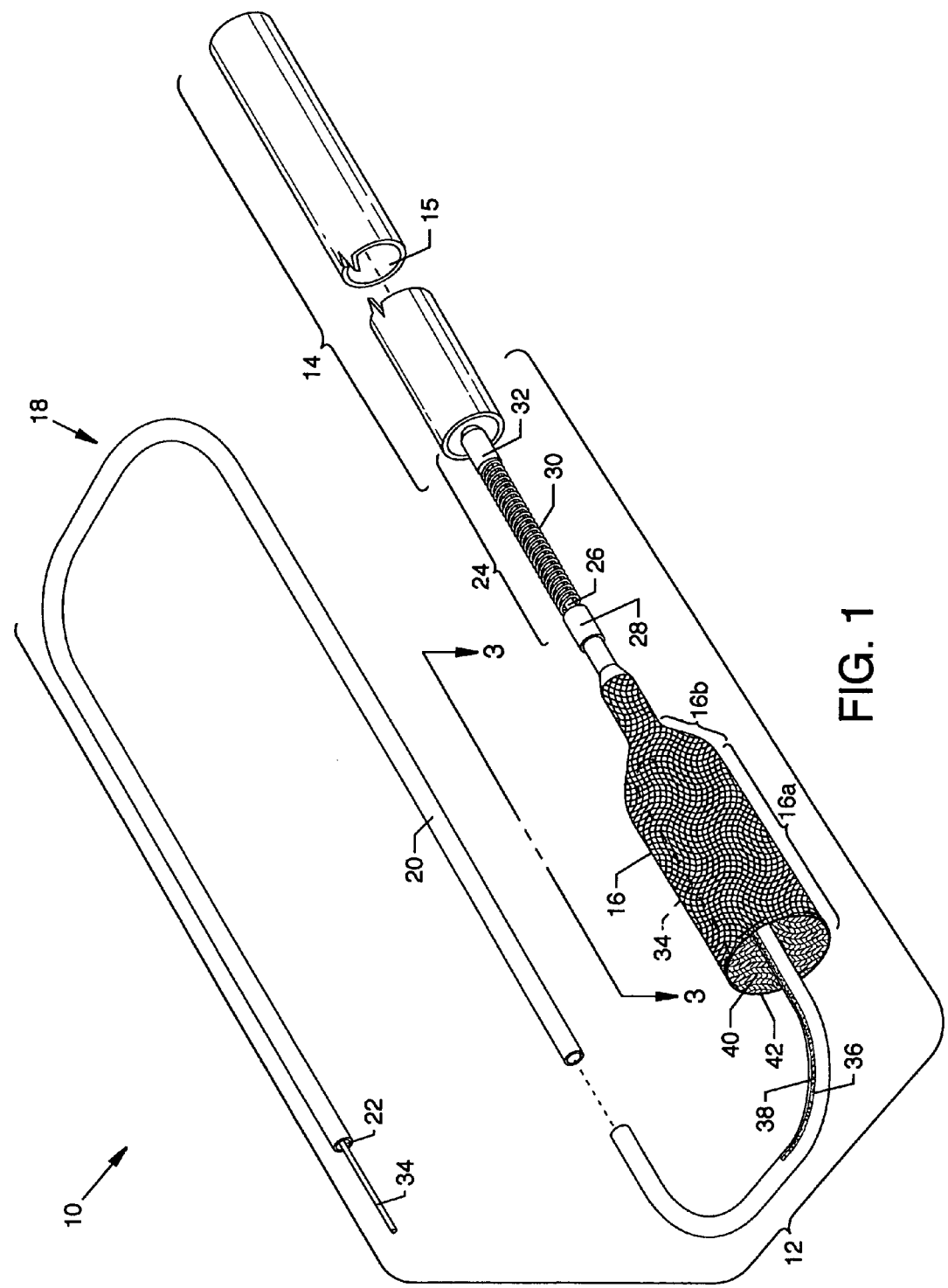
FIG. 1 is an isometric view of a guidewire with collapsible filter system, the present invention.
Figure 2:
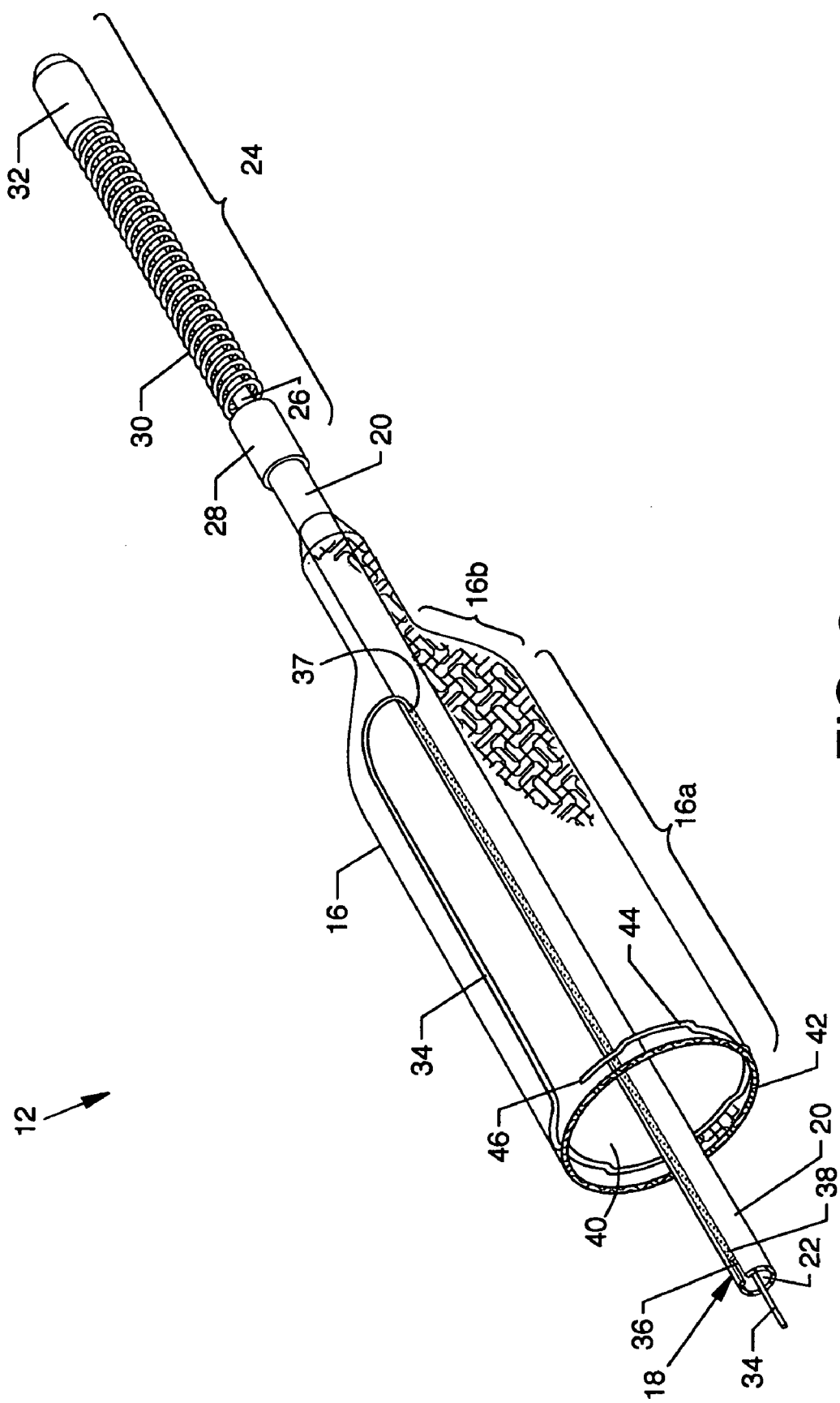
FIG. 2 is a foreshortened isometric view in cutaway of the distal portion of the guidewire with collapsible filter.
Figure 3:
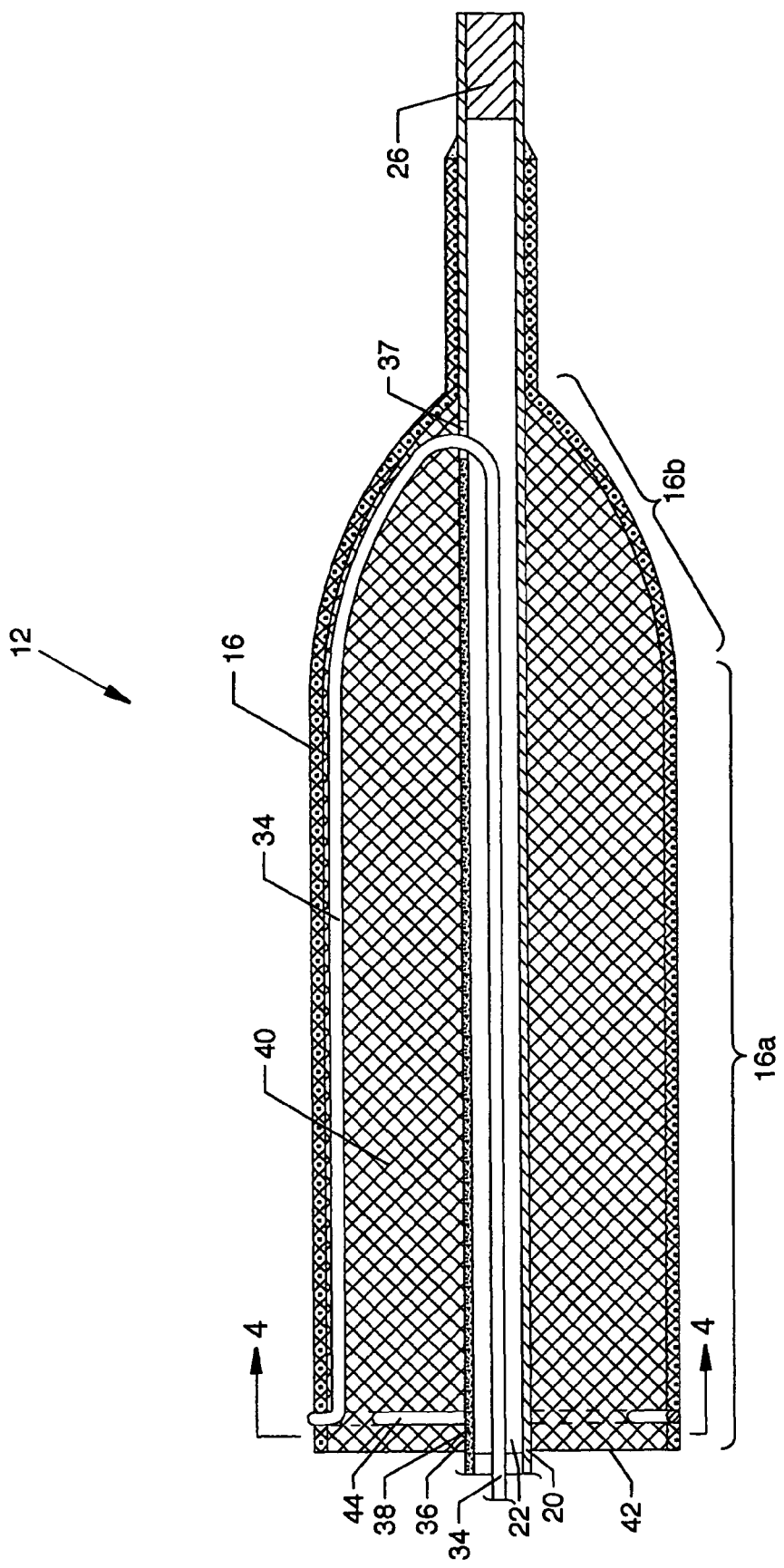
FIG. 3 is a cross section view of the distal portion of a guidewire with collapsible filter along line 3-3 of FIG. 1.

FIG. 1 is an isometric view of a guidewire with collapsible filter system 10, the present invention, including a guidewire with collapsible filter 12 and a delivery sheath 14 having a lumen 15; FIG. 2 is a foreshortened isometric view in cutaway of the distal portion of the guidewire with collapsible filter 12; and FIG. 3 is a cross section view of the distal portion of the guidewire with collapsible filter 12 along line 3-3 of FIG. 1. Best understanding of the construction and features of the present invention is achieved by referring to all of FIGS. 1, 2 and 3. One readily observed component of the invention includes a flexible and pliable collapsible filter 16 of nitinol, a nickel titanium super-elastic material belonging to a class of materials called shape memory alloys. The collapsible filter 16 is illustrated expanded in free space and forming a substantially tubular structure being open on one end and being closed on the opposing end, and more specifically, the collapsible filter 16 includes an open tubular portion 16a terminating in a closed concave portion 16b which secures over and about a guidewire tube 20 of a guidewire 18. The distal and closed end of the collapsible filter 16 secures over and about a distal portion of a guidewire tube 20 in coaxial alignment, such as by adhesive or other suitable means. The collapsible filter 16, which can be woven and which can be single or multi-layered, is co-located along and about and near the distal portion of the guidewire 18 consisting of several successively located components combined to form the guidewire 18. The guidewire 18 includes the guidewire tube 20 having a lumen 22 and a flexible tip 24 including a tapered center section 26 pluggingly secured to the distal end of the guidewire tube 20 by a weldment 28, a flexible wound spring 30 secured to the distal end of the guidewire tube 20 by the weldment 28, and a tip weldment 32 mutually securing the distal end of the tapered center section 26 and the distal end of the flexible wound spring 30. Also included as part of the guidewire 18 is a user accessible cord 34 consisting of a flexible material, such as monofilament plastic or other suitable material, extending through the lumen 22 of the guidewire tube 20 and connectingly interfacing with the proximal and other portions of the collapsible filter 16. A slot 36, which can be filled with a frangible material 38 or which may be configured in an alternative manner, extends through the wall of the guidewire tube 20 and along the guidewire tube 20 from a point near the distal end of the guidewire tube 20 to a location on the guidewire tube 20 located a short distance beyond the adjacent proximal end of the collapsible filter 16. As shown in FIG. 2, the cord 34 extends through the lumen 22 in a path from the distal end of the guidewire tube 20 where the cord is exposed and accessible, and thence freely and without restriction exits the lumen 22 at the distal end of the slot 36 where an expandable exit path 37 (FIG. 3) is provided, such as by the absence of frangible material 38 within the slot 36, or whereby such an expandable exit path 37 is provided by the absence of other restrictive configurations. Preferably, the frangible material 38 includes an adhesive material in order to provide for cohesiveness of the disrupted frangible material 38 to prevent disrupted frangible material from downstream distribution, whereby the disrupted frangible material 38 can adhesively cling to the region along the slot 36. Routing of the cord 34 through the lumen 22 and through the expandable exit path 37 minimizes the interference of the cord 34 with the filtering process and offers minimal interference if it is desirable to extend an Angiojet® within the expanded collapsible filter 16 for cleaning of the collapsible filter 16. Thence, the cord 34 extends preferably in close proximity to a narrow portion of the interior surface 40 of the collapsible filter 16 in a proximal direction to a point in close proximity to, but a short distance from, the peripheral annular edge 42 of the collapsible filter 16, where the cord 34 then extends in arcuate fashion as a loop 44 about and in nonbinding spaced and woven engagement with the mesh of the collapsible filter 16 a short distance from the annular edge 42. The distal end 46 of the loop 44 anchors, such as by the use of adhesive, ultrasonic welding, heat staking or other suitable methods, to the collapsible filter 16. Preferably, the weave of the annular edge 42 of the collapsible filter 16 can be formed or treated to ensure edge integrity.

Figure 4:
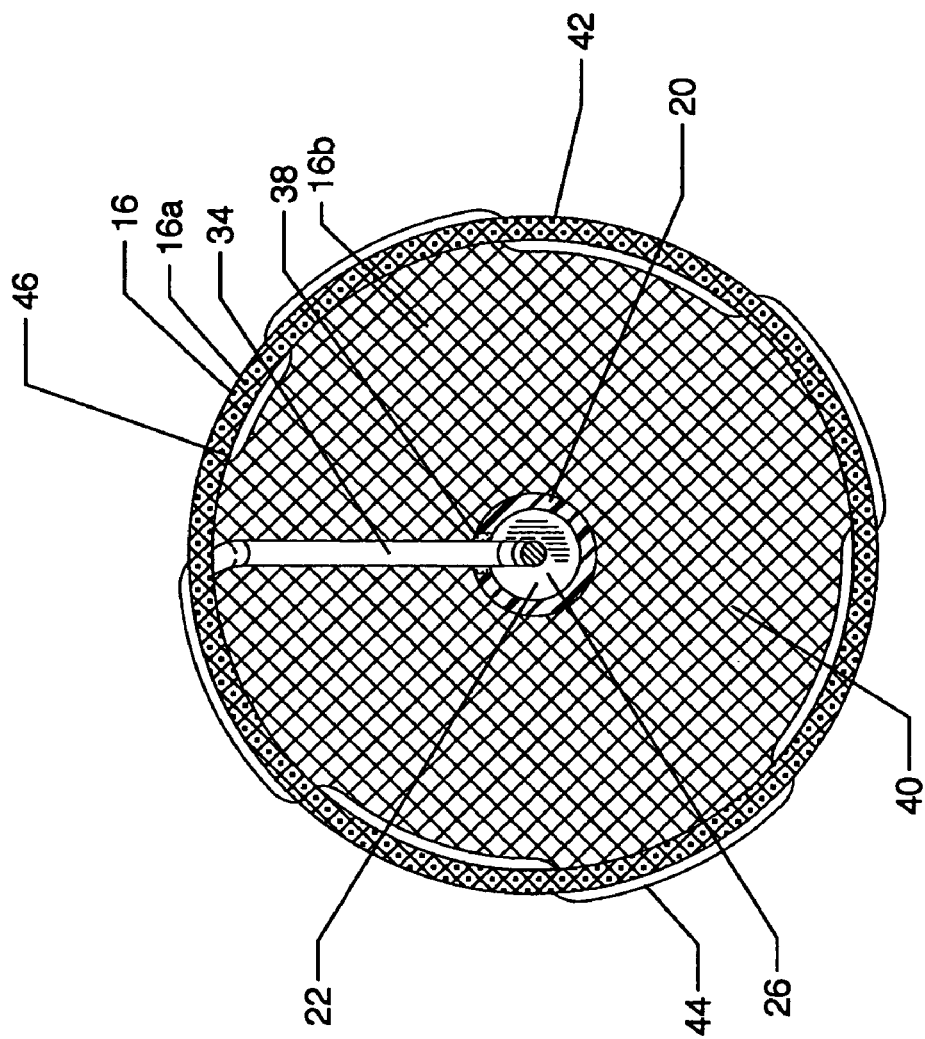
FIG. 4 is a cross section view of the guidewire with collapsible filter along line 4-4 of FIG. 3.

FIG. 4 is a cross section view of the guidewire with collapsible filter 12 along line 4-4 of FIG. 3. Shown in particular is the relationship of the cord 34 to the guidewire tube 20 and the collapsible filter 16. The cord 34 exits the lumen 22 of the guidewire tube 20 through the expandable exit path 37 (FIG. 3) and thence is directed proximally to form the loop 44 near the proximally located annular edge 42 of the collapsible filter 16.

Mode of Operation

FIGS. 5, 6, 7, 8 and 9 illustrate the mode of operation of the guidewire with collapsible filter system 10 where all or part of the distal end of the guidewire with collapsible filter system 12 is shown engaging a blood vessel 48. Generally, the overall sequence of steps utilized to operate the guidewire with collapsible filter system 10 includes the following basic steps which can be combined with other steps and procedures known to the art, but which are not referenced for the purpose of brevity and clarity. The term "thrombus" shall be used to designate thrombus, lesions, clots, plaque, or other deposits attached to the inside of a blood vessel, artery or the like. The steps with reference to the following figures include the following:

1. Preload the distal portion of the guidewire with collapsible filter 12 to align within the distal end of the delivery sheath 14. Alternatively, this can be done during the manufacturing process.
2. Advance the delivery sheath 14 with the loaded guidewire with collapsible filter 12 (the collapsible filter 16 being compressed) through the vasculature blood vessel 48 (FIG. 5) in order to position the collapsible filter 16 of the loaded guidewire with collapsible filter 12 slightly beyond a site of thrombus 50.
3. Retract the delivery sheath 14 proximally to position and expandingly and sealingly deploy and load the guidewire with collapsible filter 12 within the blood vessel 48, whereupon one of many desired procedures can be accomplished as the collapsible filter is suitably deployed to filter out thrombotic particulate while allowing blood to flow therethrough.
4. Upon completion of one or more desired procedures, collapse the collapsible filter 16 by forcibly urging the proximal end of the cord 34, in a proximal direction, thereby elongating and minimizing the profile of the collapsible filter 16.
5. Remove the guidewire 18 with collapsible filter 16 in minimized profile and the repositioned cord 34 unitarily in one step.

With this basic understanding of the operational steps involved, the function and the use of the guidewire with collapsible filter system 10 is described with reference to the following figures.

Figure 5:
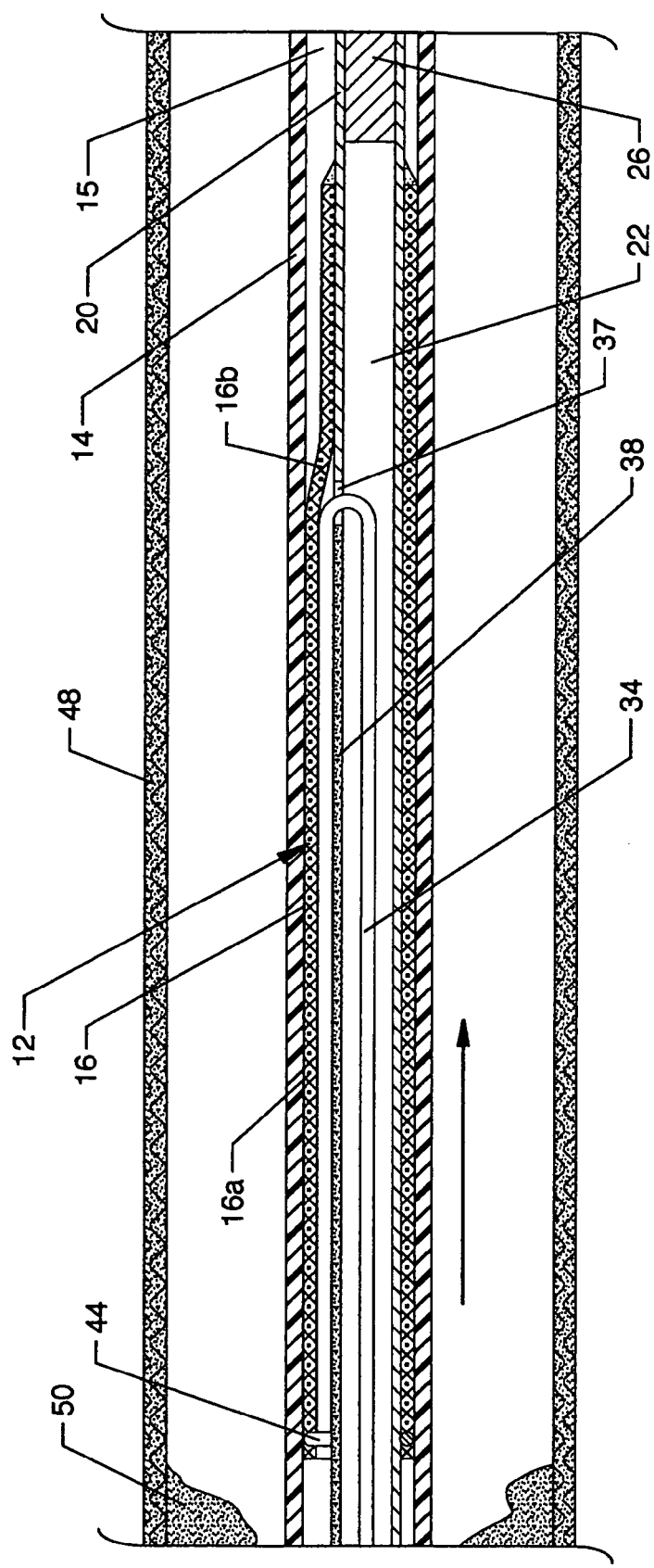
FIG. 5 is a cross section view showing the distal portion of the guidewire with collapsible filter in the compressed position aligned in and residing in the distal end portion of a lumen of a delivery sheath.

FIG. 5 is a cross section view showing the distal portion of the guidewire with collapsible filter 12 in the compressed position aligned in and residing in the distal end portion of the lumen 15 of the delivery sheath 14 where, preferably, the flexible tip 24 and closely associated structure is also located within the distal end portion of the lumen 15 of the delivery sheath 14. The delivery sheath 14 and the included distal portion of the guidewire with collapsible filter 12 are inserted into the vasculature by skills known in the art and urged unitarily to position the collapsible filter 16 a short distance beyond the region of thrombus 50 when fully deployed within the blood vessel 48.

Figure 6:
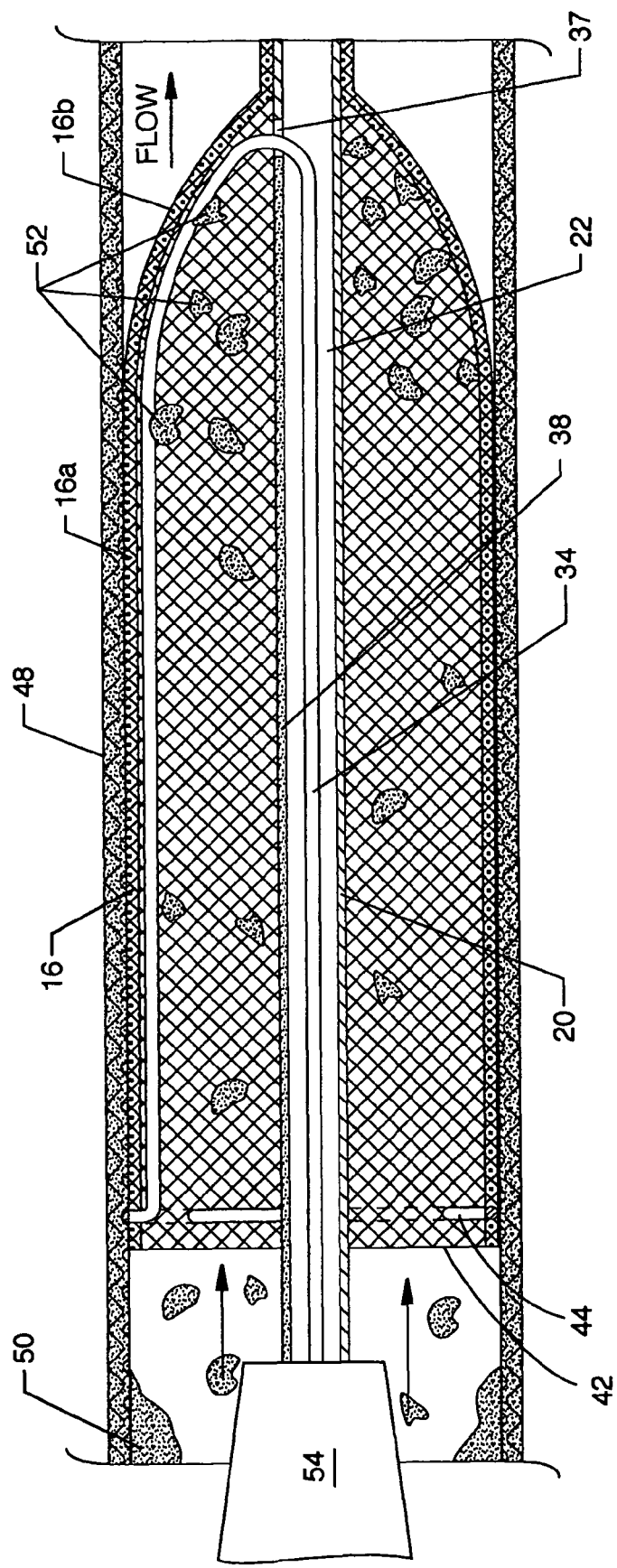
FIG. 6 is a cross section view showing the collapsible filter fully deployed in a blood vessel at a site distal to a buildup of thrombus.

FIG. 6 is a cross section view showing the collapsible filter 16 fully deployed in the blood vessel 48 at a site distal to a buildup of thrombus 50. Deployment of the collapsible filter 16 is accomplished by maintaining the position of the guidewire with collapsible filter 12 in the blood vessel 48 and then withdrawing or retracting the delivery sheath 14 a suitable distance, whereby the collapsible filter 16 is no longer under the influence of the surrounding delivery sheath 14 thus enabling the collapsible filter 16 to automatically and forcibly be deployed therefrom in outwardly directed self-expansion attempting to maintain the memory shape of the collapsible filter 16. Such expansion causes intimate conforming contact of the wall of the blood vessel 48 by the tubular portion 16a of the expanding collapsible filter 16. The concave portion 16b of the collapsible filter 16 is also expanded and presented to the oncoming flow of blood and thrombotic particulate 52, but does not come into intimate contact with the wall of the blood vessel 48. The collapsible filter 16 is then utilized in a general filtration process whereby a preponderance of errant or stray loosened thrombotic particulate 52 resulting from various procedures is filteringly trapped by the inwardly facing portion of the collapsible filter concave portion 16b. A small portion of errant or stray loosened thrombotic particulate 52 can also be deposited on the inside portion of the tubular portion 16a of the collapsible filter 16. Flowing blood passes generally through the nitinol comprising the concave portion 16b of the collapsible filter 16 to pass through the vasculature.

Figure 7:
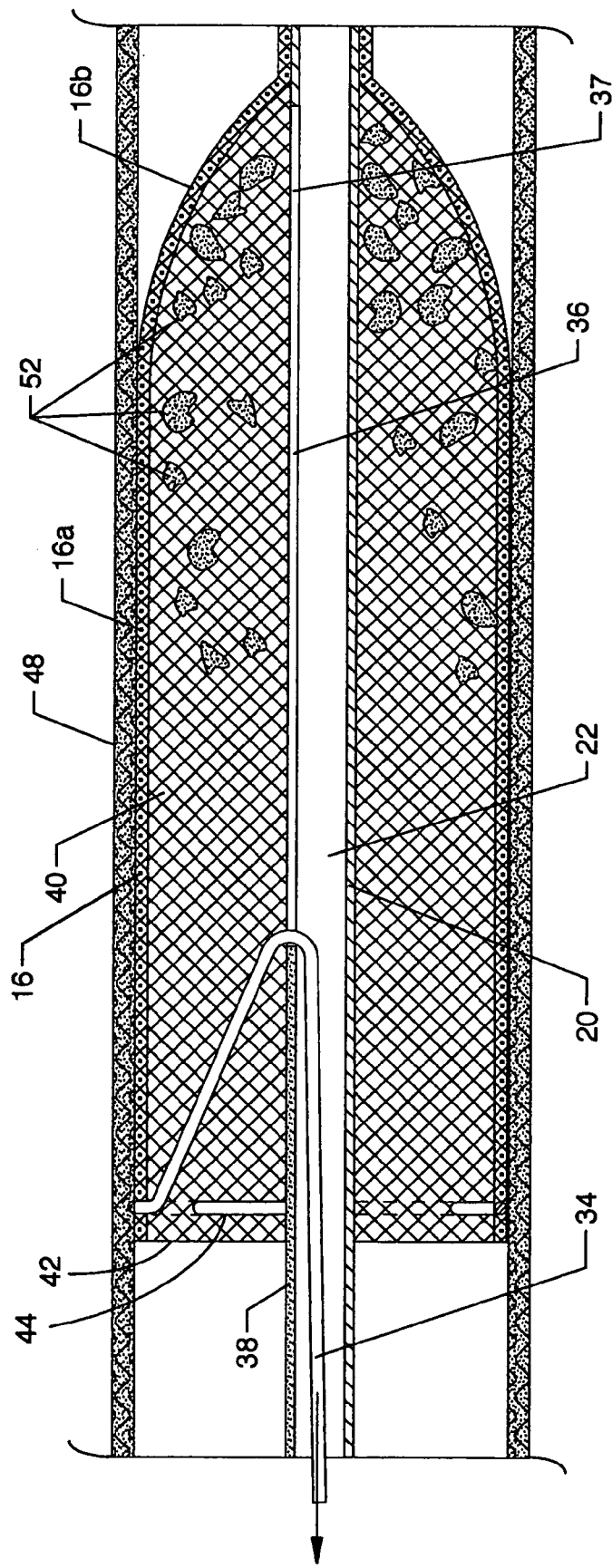
FIG. 7 is a cross section view showing the initial action involved in the parting of the frangible material by the cord and the collapsing of the collapsible filter subsequent to filtration of the thrombotic particulate by the expanded and deployed collapsible filter.

FIG. 7 is a cross section view showing the initial action involved in the parting of the frangible material 38 by the cord 34 and the collapsing of the collapsible filter 16 subsequent to filtration of the thrombotic particulate 52 by the expanded and deployed collapsible filter 16. Retraction of the collapsible filter 16 is accomplished by maintaining the position of the guidewire with collapsible filter 12 in the blood vessel 48 and then forcibly urging the exposed and accessible proximal end of the cord 34 in a proximal direction, thereby continually repositioning and utilizing a region of impinging contact of the cord 34 with the frangible material 38 causing the frangible material 38 to progressively part, thereby allowing further directed repositioning of the point of contact between the cord 34 and the frangible material 38 in a proximal direction. Other suitably constructed geometrically configured partable structure arrangements or suitable configurations can be incorporated in lieu of the slot 36 and frangible material 38 residing in the slot 36, whereby the cord 34 is sheathed within the distal end of the guidewire tube 20 until reaching a desirable exit path similar in many respects to the expandable exit path 37.

Figure 8:
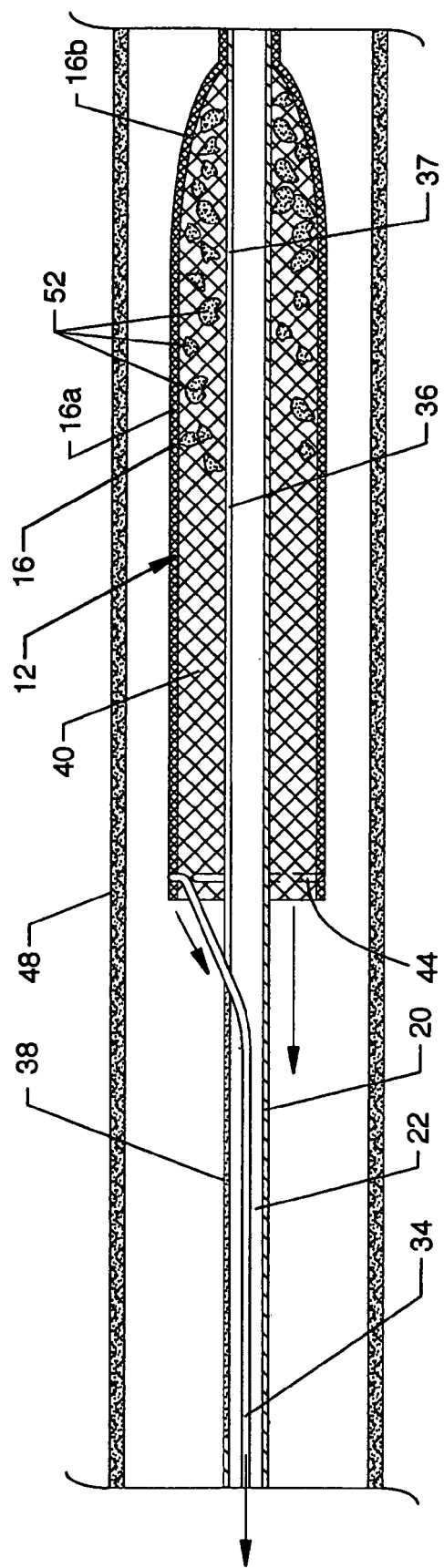
FIG. 8 is a cross section view showing the cord forcibly actuated further in a proximal direction along the lumen and the slot of the guidewire tube causing further parting of the frangible material.

FIG. 8 is a cross section view showing the cord 34 forcibly actuated further in a proximal direction along the lumen 22 and the slot 36 causing further parting of the frangible material 38, whereby the collapsible filter 16 is partially elongated, thus partially reducing the profile and cross section thereof. During the elongation of the collapsible filter 16, the loop 44 woven peripherally about, through and within the nitinol mesh near the proximal end of the collapsible filter 16 weavingly cinches along, about and through the proximal region of the collapsible filter 16 and transfers and is increasingly instrumental in distributing the proximally directed force of the cord 34 along and about the length of the collapsible filter 16. During such forcible elongation and reduction of the profile of the collapsible filter 16, the thrombotic particulate 52, having a compressible consistency, may be compacted by the diminishing profile of the collapsible filter 16, such as shown in FIG. 9.

Figure 9:
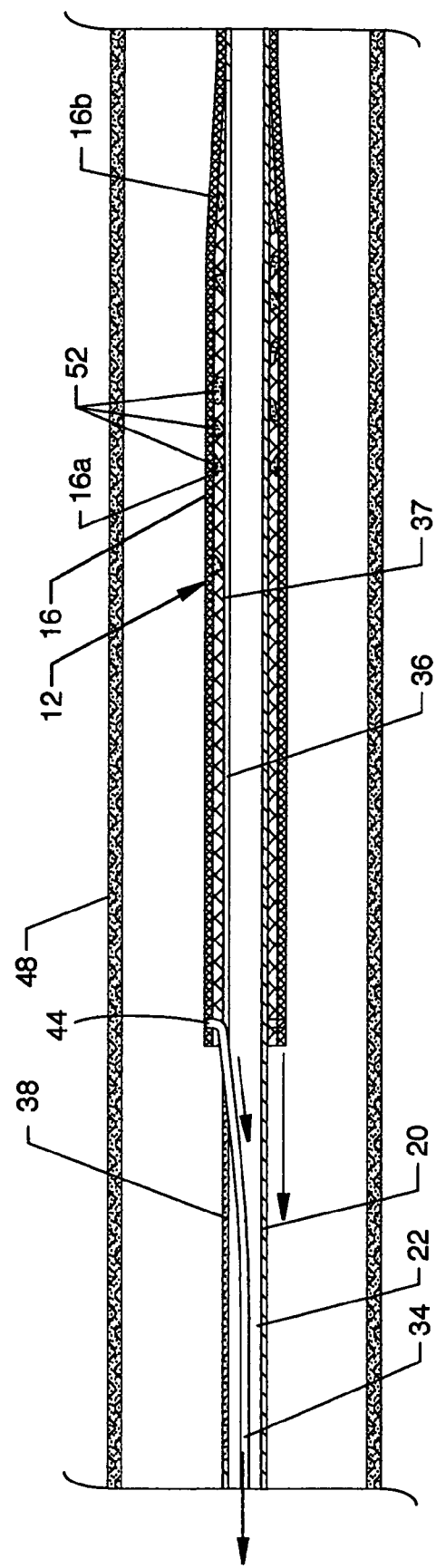
FIG. 9 is a cross section view showing the cord having been maximally and forcibly actuated further in a proximal direction along the lumen and the slot of the guidewire tube, whereby the collapsible filter is fully elongated and has a minimum profile or cross section; and, FIG. 10 is a cross section view showing the optional use of a thrombectomy catheter (Angiojet®) with the present invention for the purpose of cleansing of the collapsible filter.

FIG. 9 is a cross section view showing the cord 34 having been maximally and forcibly actuated further in a proximal direction along the lumen 22 and the slot 36, whereby the collapsible filter 16 is fully elongated and has a minimum profile and cross section. When such a configuration is achieved, the guidewire with collapsible filter 12 can be removed in a collapsed unitary fashion whereby the proximally directed force along the cord 34 is maintained relative to the guidewire tube 20 in order to maintain the minimum cross section of the collapsible filter 16 containing the thrombotic particulate 52 during retraction. Optionally, the delivery sheath 14 or other suitable device can be incorporated to assist in removal through the insertion wound.

Additionally, during or prior to removal of the guidewire with collapsible filter 12, fluid flow can be maintained by the simultaneous use of a thrombectomy catheter 54 (shown in other use in FIG. 10) at a location proximal to the collapsible filter 16 in unitary withdrawal fashion to exhaust errant or other thrombotic particulate 52 stopped by the collapsible filter 16 to prevent flow of errant thrombotic particulate 52 distally along the vasculature. In the alternative, suction may be applied to the thrombectomy catheter 54 to assist in removal of thrombotic particulate 52.

Figure 10:
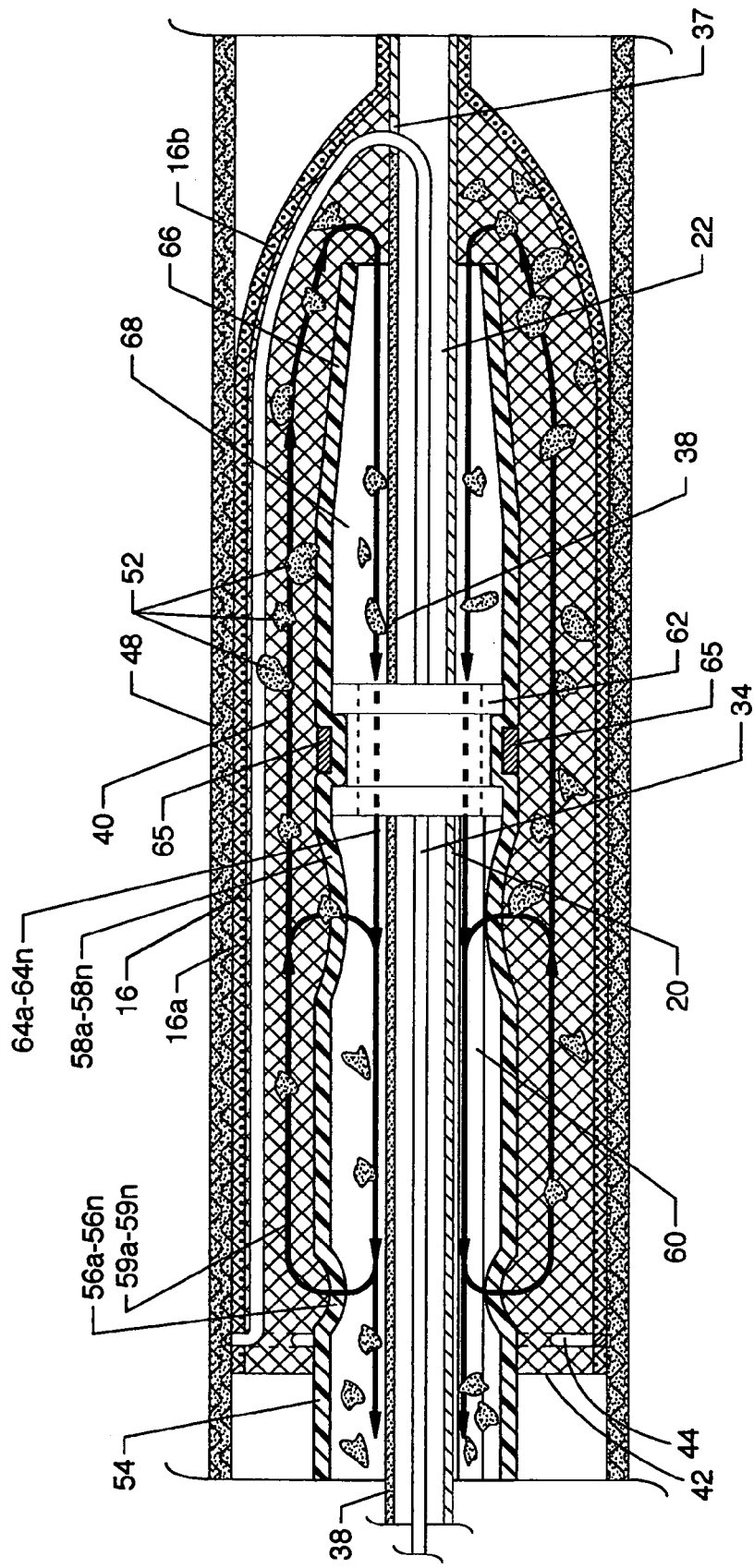

FIG. 10 is a cross section view showing the optional use of the thrombectomy catheter 54 (Angiojet®) with the present invention for the purpose of cleansing the collapsible filter 16, should it be desired to remove excess thrombotic particulate 52 from the collapsible filter 16. Cleansing of thrombotic particulate 52 from the collapsible filter 16 can be desirable if excess thrombotic particulate 52 impedes the flow of blood through the collapsible filter 16 and thus the blood vessel 48, and can also be desirable if excess thrombotic particulate 52 may impede the collapsing of the collapsible filter 16 to a minimum profile. The thrombectomy catheter 54, the subject of other patents by the applicant, includes a plurality of outflow orifices 56a-56n and inflow orifices 58a-58n through which cross stream flows 59a-59n of saline solution or other suitable ablation medium passes to break up thrombus 50. Also shown residing in the thrombectomy catheter 54 is a high pressure tube 60 and a connected fluid jet emanator 62 for the emanation of high pressure fluid jets 64a-64n. A radiopaque marker band 65 is also incorporated with the thrombectomy catheter 54. Also illustrated is the positioning of the distal tip 66 of the thrombectomy catheter 54 in close proximity to the concave portion 16b of the collapsible filter 16. The fluid jets 64a-64n are emitted from the fluid jet emanator 62 to pass outwardly from the outflow orifices 56a-56n in circulatory cross stream flows 59a-59n re-entering at multiple locations, including the inflow orifices 58a-58n, and distally at the inlet of the distal tip 66, whereby the flow urges, dislodges and dispels the thrombotic particulate 52 from the tubular portion 16a and from the concave portion 16b of the collapsible filter 16 to be evacuated in a proximal direction with the flow through a central lumen 68 of the thrombectomy catheter 54.

Various modifications can be made to the present invention without departing from the apparent scope thereof.

GUIDEWIRE WITH COLLAPSIBLE FILTER SYSTEM AND METHOD OF USE

Parts List 10 guidewire with collapsible filter system
12 guidewire with collapsible filter
14 delivery sheath
15 lumen
16 collapsible filter
16a tubular portion
16b concave portion
18 guidewire
20 guidewire tube
22 lumen
24 flexible tip
26 tapered center section
28 weldment 30 flexible wound spring
32 tip weldment
34 cord
36 slot
37 expandable exit path
38 frangible material
40 interior surface
42 annular edge
44 loop
46 distal end
48 blood vessel
50 thrombus
52 thrombotic particulate
54 thrombectomy catheter
56a-n outflow orifices
58a-n inflow orifices
59a-n cross stream flows
60 high pressure tube
62 fluid jet emanator
64a-n fluid jets
65 radiopaque marker band
66 distal tip
68 central lumen

The invention claimed is:

1. A guidewire with a collapsible filter comprising:
  a. the guidewire having a tubular distal portion, the tubular distal portion having a distal portion, a longitudinal slot in a wall of the tubular distal portion, the slot further containing a frangible material and an exit path at the distal portion;
  b. the collapsible filter being made of a flexible fine mesh material secured over and about the tubular distal portion of the guidewire, the collapsible filter having a length from a proximal end to a distal end, the distal end of the collapsible filter being attached to the tubular distal portion of the guidewire;
  c. the collapsible filter exhibits shape memory, whereby such a shape is compressibly suitable for automatic expansion from within a delivery sheath;
  d. a flexible cord passing through the slot and exiting at the exit path at the distal end of the filter and running along the length of the filter from the distal end to the proximal end and only attaching to the proximal end of the collapsible filter; and
  e. the guidewire, the collapsible filter, and the flexible cord being configured so that tension applied to the flexible cord causes the collapsible filter to be drawn towards a collapsed configuration.

2. The guidewire with collapsible filter of claim 1, further comprising a delivery sheath which restrains the collapsible filter in a collapsed configuration for introduction and advancement.

3. The guidewire with collapsible filter of claim 1, wherein the memory shape is an expanded configuration so that when unrestrained the collapsible filter tends to expand and apply conforming and sealing forces on a vessel or passage wherein it is located.

4. The guidewire with collapsible filter of claim 3, wherein the collapsible filter is configured to allow passage of blood and smaller particles while filtering and capturing larger particles.

5. The guidewire with collapsible filter of claim 1, wherein the slot is elongated.

6. The guidewire with collapsible filter of claim 1, further comprising a retrieval catheter into which the collapsible filter is drawn.

7. The guidewire with collapsible filter of claim 1, further comprising a thrombectomy catheter for removal of filtered particles.

8. A thrombectomy catheter comprising:
  a catheter body extending from a catheter distal portion toward a catheter proximal portion, the catheter body including a catheter lumen;
  a high pressure tube extending through the catheter lumen from the catheter proximal portion toward the catheter distal portion, the high pressure tube in communication with a fluid source near the catheter proximal portion;
  a fluid jet emanator in communication with the high pressure tube, the fluid jet emanator configured to produce a fluid jet within the catheter lumen;
  a plurality of outflow and inflow orifices on the catheter body working in cooperation with the fluid jet to produce circulatory cross stream flows of fluid; and
  a guidewire with a collapsible filter further comprising a tubular distal portion having a distal portion, a longitudinal slot in a wall of the tubular distal portion, the slot further containing a frangible material and an exit path at the distal portion; the collapsible filter being made of a flexible fine mesh material secured over and about the tubular distal portion of the guidewire, the collapsible filter having a length from a proximal end to a distal end, the distal end of the collapsible filter being attached to the tubular distal portion of the guidewire; the collapsible filter exhibits shape memory, whereby such a shape is compressibly suitable for automatic expansion from within a delivery;
  a flexible cord passing through the slot and exiting at the exit path at the distal end of the filter and running along the length of the filter from the distal end to the proximal end and only attaching to the proximal end of the collapsible filter; and the guidewire, the collapsible filter, and the flexible cord being configured so that tension applied to the flexible cord causes the collapsible filter to be drawn towards a collapsed configuration.

9. The thrombectomy catheter of claim 8, further comprising a delivery sheath which restrains the collapsible filter in a collapsed configuration for introduction and advancement.

10. The thrombectomy catheter of claim 8, wherein the memory shape is an expanded configuration so that when unrestrained the collapsible filter tends to expand and apply conforming and sealing forces on a vessel or passage wherein it is located.

11. The thrombectomy catheter of claim 8, further comprising a retrieval catheter into which the collapsible filter is drawn.

* * * * *

UNITED STATES PATENT AND TRADEMARK OFFICE
CERTIFICATE OF CORRECTION

PATENT NO. : 7,846,175 B2
APPLICATION NO. : 11/396732
DATED : December 7, 2010
INVENTOR(S) : Bonnette et al.

It is certified that error appears in the above-identified patent and that said Letters Patent is hereby corrected as shown below:

ON THE TITLE PAGE

Item (54), in Title, Line 1, delete "GUIDEWIRE AND COLLAPSABLE" and insert -- GUIDEWIRE WITH COLLAPSIBLE --, therefor.

On Title Page 3, Item (56), under "OTHER PUBLICATIONS", in Column 2, Line 3, delete "Arteries"." and insert -- Arteries", --, therefor.

In Column 1, Line 1, delete "GUIDEWIRE AND COLLAPSABLE" and insert -- GUIDEWIRE WITH COLLAPSIBLE --, therefor.

In Column 5, Line 28, delete "guidewire and collapsible" and insert -- guidewire with collapsible --, therefor.

In Column 10, Line 51, after "SYSTEM" delete "AND METHOD OF USE".

IN THE CLAIMS

In Column 12, Line 26, delete "and", therefor.

In Column 12, Line 39, insert -- sheath; and -- after "delivery", therefor.

Signed and Sealed this
Third Day of January, 2012

David J. Kappos
*Director of the United States Patent and Trademark Office*